(12) United States Patent
Cronin et al.

(10) Patent No.: US 10,366,206 B2
(45) Date of Patent: Jul. 30, 2019

(54) SYSTEM AND METHOD FOR PROVIDING CONNECTING RELATIONSHIPS BETWEEN WEARABLE DEVICES

(71) Applicant: KONINKLIJKE PHILIPS N.V., Eindhoven (NL)

(72) Inventors: John Cronin, Bonita Springs, FL (US); Joseph George Bodkin, Fort Meyers, FL (US); Jan Martijn Krans, Den Bosch (NL); Boris Emmanuel Rachmund De Ruyter, Peer (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 15/527,340

(22) PCT Filed: Dec. 2, 2015

(86) PCT No.: PCT/EP2015/078266
§ 371 (c)(1),
(2) Date: May 17, 2017

(87) PCT Pub. No.: WO2016/087476
PCT Pub. Date: Jun. 9, 2016

(65) Prior Publication Data
US 2017/0351828 A1    Dec. 7, 2017

Related U.S. Application Data

(60) Provisional application No. 62/087,699, filed on Dec. 4, 2014.

(30) Foreign Application Priority Data

May 26, 2015  (EP) .................................. 15169210

(51) Int. Cl.
*A61B 5/00* (2006.01)
*A61B 5/0205* (2006.01)
(Continued)

(52) U.S. Cl.
CPC ........ *G06F 19/3418* (2013.01); *A61B 5/0024* (2013.01); *A61B 5/0205* (2013.01);
(Continued)

(58) Field of Classification Search
CPC ........ G06F 19/3418; H04W 4/80; H04W 4/38
See application file for complete search history.

(56) References Cited

U.S. PATENT DOCUMENTS

| 4,446,871 A | 5/1984 | Imura |
|---|---|---|
| 5,435,309 A | 7/1995 | Thomas |

(Continued)

FOREIGN PATENT DOCUMENTS

WO    2014/169390    10/2014

OTHER PUBLICATIONS

Arshak, et al., "Modelling and simulation of wireless sensor system for health monitoring using HDL and Simulink mixed environment", IET Comput. Digit. Tech., 2007, 1, (5), pp. 508-518.

*Primary Examiner* — Muhammad N Edun
*Assistant Examiner* — Jerold B Murphy

(57) ABSTRACT

A computer-implemented method or system is provided for providing connecting relationships between wearable devices. The method includes measuring a first health parameter of a user via one or more sensors of a first wearable device; measuring a second health parameter of the user via one or more sensors of a second wearable device; determining an alert action based on a combination of the measurements of first health parameter and the second health parameter; and generating a notification to the user based on the alert action.

13 Claims, 16 Drawing Sheets

(51) Int. Cl.

| | | |
|---|---|---|
| *G06F 19/00* | (2018.01) | |
| *H04W 4/70* | (2018.01) | |
| *G16H 50/20* | (2018.01) | |
| *G06Q 10/10* | (2012.01) | |
| *H04W 4/08* | (2009.01) | |
| *H04Q 9/00* | (2006.01) | |
| *A61B 5/01* | (2006.01) | |
| *A61B 5/024* | (2006.01) | |
| *A61B 5/08* | (2006.01) | |
| *A61B 5/11* | (2006.01) | |
| *A61B 5/145* | (2006.01) | |
| *H04W 84/20* | (2009.01) | |
| *H04W 4/38* | (2018.01) | |

(52) U.S. Cl.
CPC ............ *A61B 5/6802* (2013.01); *A61B 5/746* (2013.01); *G06Q 10/10* (2013.01); *G16H 50/20* (2018.01); *H04Q 9/00* (2013.01); *H04W 4/08* (2013.01); *H04W 4/70* (2018.02); *A61B 5/01* (2013.01); *A61B 5/024* (2013.01); *A61B 5/0816* (2013.01); *A61B 5/1118* (2013.01); *A61B 5/1123* (2013.01); *A61B 5/14532* (2013.01); *H04Q 2209/823* (2013.01); *H04W 4/38* (2018.02); *H04W 84/20* (2013.01)

(56) References Cited

U.S. PATENT DOCUMENTS

| | | | |
|---|---|---|---|
| 6,812,845 | B2 | 11/2004 | Yuzuki |
| 2003/0063003 | A1 | 4/2003 | Bero |
| 2004/0062133 | A1 | 4/2004 | Tsuji |
| 2004/0098144 | A1* | 5/2004 | Hashimoto ............ A61B 5/11 700/27 |
| 2012/0203491 | A1* | 8/2012 | Sun ...................... A61B 5/0006 702/108 |
| 2014/0218184 | A1 | 8/2014 | Grant |
| 2014/0243622 | A1 | 8/2014 | Crowe |
| 2014/0267299 | A1 | 9/2014 | Couse |
| 2014/0275852 | A1 | 9/2014 | Hong |
| 2014/0300490 | A1* | 10/2014 | Kotz ................... A61B 5/0028 340/870.3 |
| 2015/0065055 | A1 | 3/2015 | Newham |
| 2015/0201859 | A1* | 7/2015 | Baker ................. A61B 5/0456 600/324 |

* cited by examiner

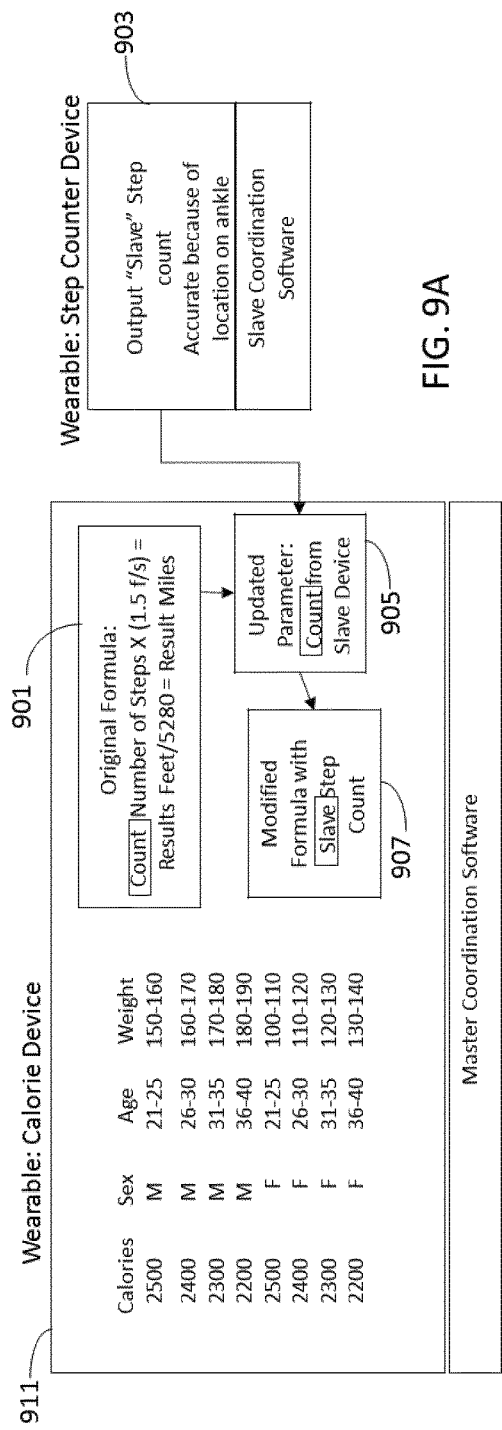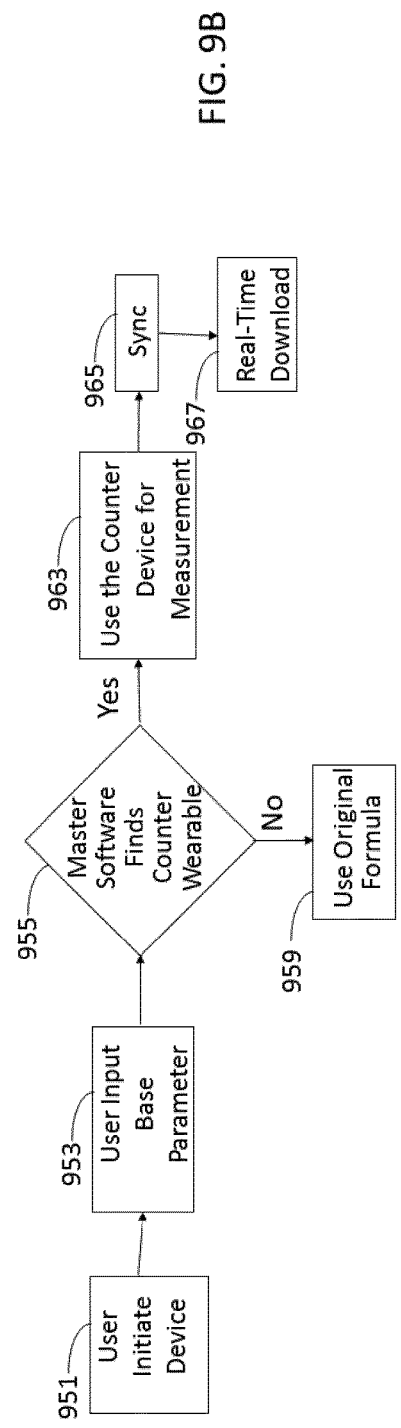

SYSTEM AND METHOD FOR PROVIDING CONNECTING RELATIONSHIPS BETWEEN WEARABLE DEVICES

CROSS REFERENCE TO RELATED APPLICATIONS

This application is the U.S. National Phase application under 35 U.S.C. § 371 of International Application No. PCT/EP2015/078266, filed Dec. 2, 2015, published as WO 2016/087476 on Jun. 9, 2016, which claims the benefit of U.S. Provisional Patent Application No. 62/087,699 filed Dec. 4, 2014 and European Patent Application Number 15169210.0 filed May 26, 2015. These applications are hereby incorporated by reference herein.

FIELD OF THE INVENTION

The present invention generally relates to wearable devices. More specifically, the present invention relates to data collection, transmission and processing for providing connecting relationships between the wearable devices.

BACKGROUND OF THE INVENTION

Wearable technology is a new class of electronic systems that can provide data acquisition through a variety of unobtrusive sensors that may be worn by a user. The sensors gather information, for example, about the environment, the user's activity, or the user's health status. However, there are significant challenges related to the coordination, computation, communication, privacy, security, and presentation of the collected data.

Additionally, there are challenges related to power management given the current state of battery technology. Furthermore, analysis of the data is needed to make the data gathered by the sensors useful and relevant to end-users. In some cases, additional sources of information may be used to supplement the data gathered by the sensors. The many challenges that wearable technology presents require new designs in hardware and software.

The advantages of the wearable device include its proximity to the user and consistency of its computations. For example, a number of wearable devices, while worn by the user, constantly and continuously monitor user's data and/or vital signs of the user. Such information can be useful in subsequent analysis of condition and behavior of the user and/or can be used for performing an action necessitated by the measurements.

However, the constant monitoring of the user's data can reduce the flexibility of the measurements that wearable device can perform, which can lead to undesirable conclusions.

SUMMARY OF THE CLAIMED INVENTION

It is an object of some embodiments of an invention to disclose a system and a method for providing connecting relationships between wearable devices. As used herein, the term "wearable" broadly encompasses devices associated with the user, e.g. worn over or attached to a body part, or embedded into an item of clothing or footwear, and configured for either contact or non-contact sensing of various health parameters through a number of approaches. For example, heart rate can be measured via photoplethysmography or bioimpedance measurements.

As used herein, the health parameter can include any vital sign including, but not limited to a blood pressure, a hydration level, a calorie rate, a blood sugar level, a blood glucose level, an insulin level, a weight level, a sleep measurement, a number of steps, a body temperature, a heart rate, a heart sound, a respiratory rate, a breathing sound, a movement speed, a skin moisture, a sweat level, a sweat composition, or a nerve firing.

Some embodiments of the invention are based on recognition that there are many wearable devices, and some are better than others in the measurement under various circumstances. For example a pedometer worn on the foot of the user is more effective at counting steps than a pedometer worn on the arm. On the other hand, an activity monitor worn on the arm is more effective for pulse scanning.

Additionally or alternatively, some embodiments are based on recognition that different wearable devices can measure the same or different health parameters of the user in order to cooperatively determine the necessity to alert the user about, e.g., a potential danger. For example, one wearable device can measure the blood pressure when the other wearable device can measure the number and/or the rate of steps made by the user for a period of time. Those two measurements of the health parameters can be cooperatively used to better inform the user.

For example, in one embodiment, the wearable devices form a master-slave relationship. In this embodiment, one of the wearable devices is assigned to a master role and performs the comparison of the health parameters instead of having this performed by a third device (e.g., smartphone). This embodiment thus has one less device connected to the system and thus less power consumed by the system. In alternative embodiment, the comparison is performed by a third device, e.g., a smartphone. In this embodiment, both wearable devices assigned to the slave role. Additionally or alternatively, the master-slave relationship can connect a master device with a plurality of slaves. To better address this concern, a first aspect includes a computer-implemented method for providing connecting relationships between wearable devices, the method includes measuring a first health parameter of a user via one or more sensors of a first wearable device; measuring a second health parameter of the user via one or more sensors of a second wearable device; determining an alert action based on a combination of the measurements of first health parameter and the second health parameter; and generating a notification to the user based on the alert action. A further aspect of the invention provides a system for providing connecting relationships between wearable devices, the system includes a first wearable device including one or more sensors configured to measure a first health parameter of a user wearing the first wearable device; a transceiver configured to receive a measurement of a second health parameter of the user over a wireless communication network; and a processor configured to determine an alert action based on a combination of the measurements of the first health parameter and the second health parameter, and further configured to generate a notification to the user based on the alert action.

A further aspect of the invention provides a non-transitory computer-readable storage medium, having embodied thereon a program executable by a processor to perform a method for providing on-demand wireless services, the method comprising measuring one or more base parameters via one or more sensors of a first device; determining that the measurement of the base parameter meets a certain predetermined criterion; requesting one or more additional measurements from one or more secondary devices; determining an alert action based on a combination of measurements of the base parameters and additional measurements received from the secondary devices; and generating a notification to the user based on the alert action.

Preferred embodiments of the disclosure are defined in the dependent claims. It should be understood that the claimed computer-implemented method, the system for providing connecting relationships between wearable devices, and the claimed non-transitory computer readable storage medium can have similar preferred embodiments and the corresponding advantages as the claimed method and as defined in the dependent method claims.

Therefore, a need in the art for improved systems and methods of providing a connecting relationship between wearable devices measuring health parameters is achieved.

BRIEF DESCRIPTION OF THE DRAWINGS

FIG. 9A illustrates an implementation of an exemplary coordination method for providing connecting relationships among wearable devices according to an embodiment of the present invention.

FIG. 9B shows a flowchart illustrating an exemplary coordination method for providing connecting relationships among wearable devices according to an embodiment of the present invention.

DETAILED DESCRIPTION

Several embodiments of the invention with reference to the appended drawings are now explained. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Reference in the specification to "one embodiment" or "an embodiment" means that a particular feature, structure, or characteristic described in conjunction with the embodiment can be included in at least one embodiment of the invention. The appearances of the phrase "in one embodiment" in various places in the specification do not necessarily all refer to the same embodiment.

Figure 1:
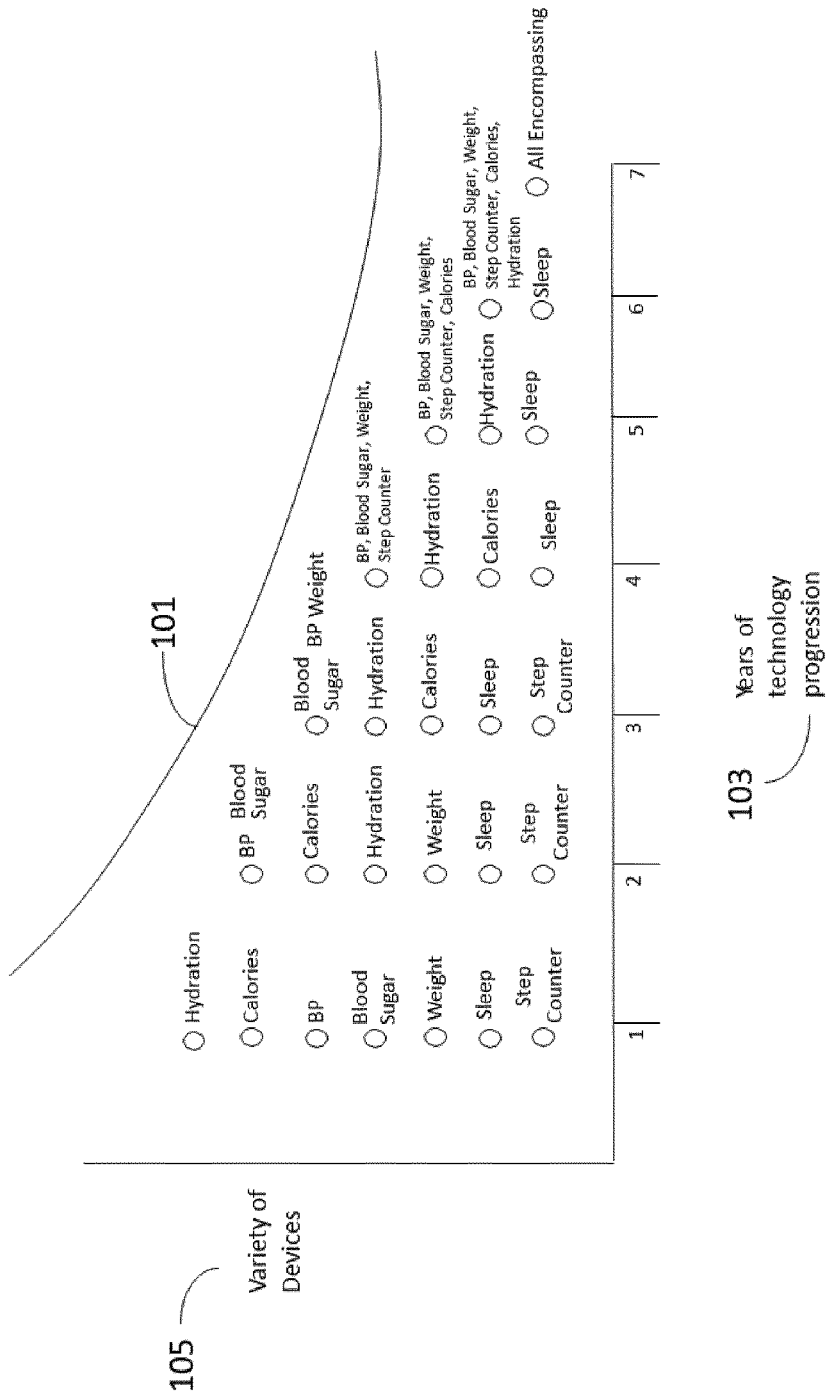
FIG. 1 illustrates a variety of wearable devices measuring a variety of parameters in an exemplary system for providing connecting relationships among wearable devices according to an embodiment of the present invention.

FIG. 1 illustrates a variety of wearable devices measuring a variety of health parameters of a user wearing the wearable devices. Such parameters may include hydration, calories, blood pressure, blood sugar or glucose, insulin, body temperature (i.e., thermometer), heart rate, weight, sleep, number of steps (i.e., pedometer), velocity or acceleration (i.e., accelerometer), vitamin levels, respiratory rate, heart sound (i.e., microphone), breathing sound (i.e., microphone), movement speed, skin moisture, sweat detection, sweat composition, nerve firings (i.e., electromagnetic sensor), or similar health measurements. In some embodiments, additional sensors may also measure allergens, air quality, air humidity, air temperature, and similar environmental measurements. Some of the parameters may further be integrated in various combination (e.g., blood pressure and sugar together). Some wearable devices (e.g., Apple watch) may have multiple different sensors for monitoring different parameters.

These wearable devices in FIG. 1 are pictured underneath a curve 101 along a chart, where one axis of the chart shows years of technology progression 103 and the other axis of the chart shows a variety of devices 105. The chart endeavors to illustrate an exemplary hypothetical progression of wearable technology, and indicates that as technology progresses, fewer wearable devices may be needed to measure a variety of parameters.

Figure 2:
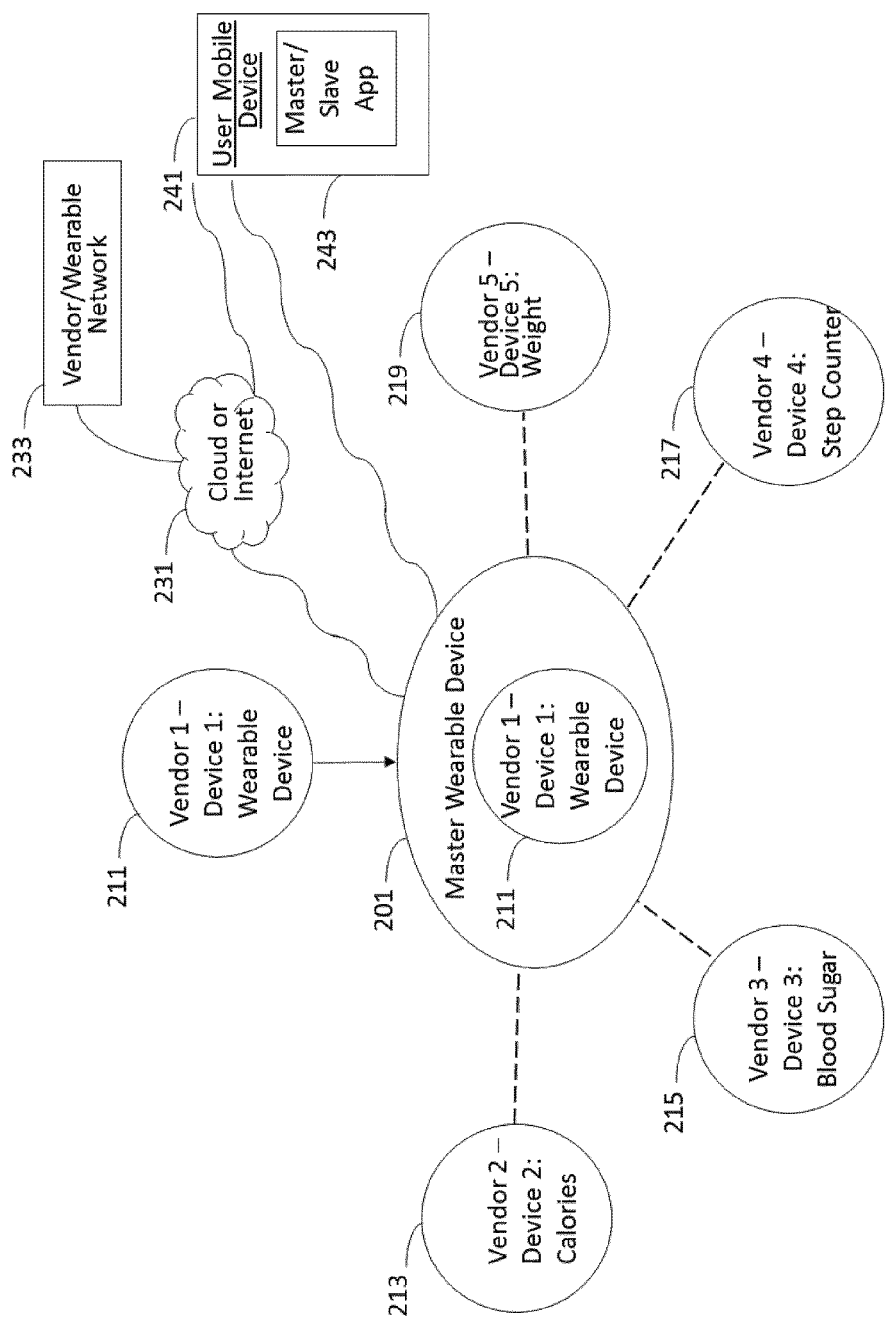
FIG. 2 illustrates a network environment in which an exemplary system for providing connecting relationships among wearable devices may be implemented according to an embodiment of the present invention.

FIG. 2 illustrates a network environment in which an exemplary system for providing connecting relationships among wearable devices is implemented by one embodiment of the invention. As illustrated, the wearable devices (211, 213, 215, 217, and 219) may be made or sold from a variety of vendors, thereby having different sensors and functions (e.g., measuring calories, blood sugar, steps, weight). Each device may be assigned a master or slave role, as well as connect via the cloud/internet 231 to a user mobile device 241, e.g., a smartphone running a master-slave application 243 and a vendor/wearable network server 233.

For example, vendor one may be associated with master device one 211, vendor two may be associated with slave device two 213 that measures calories, vendor three may be associated with slave device three 215 that measures blood sugar, vendor four may be associated with slave device four 217 that counts steps, and vendor five may be associated with slave device five 219 that tracks weight, etc. Each device may have a corresponding master-slave application configured based on their respective roles. In FIG. 2, the master role of master device one 211 is indicated by circle 201.

Roles (i.e., the master role 201 or the slave roles) may be assigned based on a variety of factors, including the capabilities of the wearable devices. Some wearable devices may only be capable of working as slaves, outputting their data to the master wearable device on request. Some devices capable of being masters may be slaves where there is another master device that is better-suited for the master role 201. The master role 201 may, in some embodiments, shift from a first wearable device to a second wearable device at a particular time, depending on which wearable device is best suited for the master role 201 at the current time.

The vendor/wearable network 233 may include one or more servers and may provide information regarding the respective wearable devices, which may be used to determine which the best master-slave is or how to configure the master-slave relationships.

In some embodiments, the vendor/wearable network 233 may be tied to a single wearable device, multiple wearable devices by a single vendor, or multiple wearable devices by multiple vendors. In some embodiments, the vendor/wearable network 233 comprises a variety of individual vendor networks and/or wearable networks connected through the cloud/internet 231.

Figure 3:
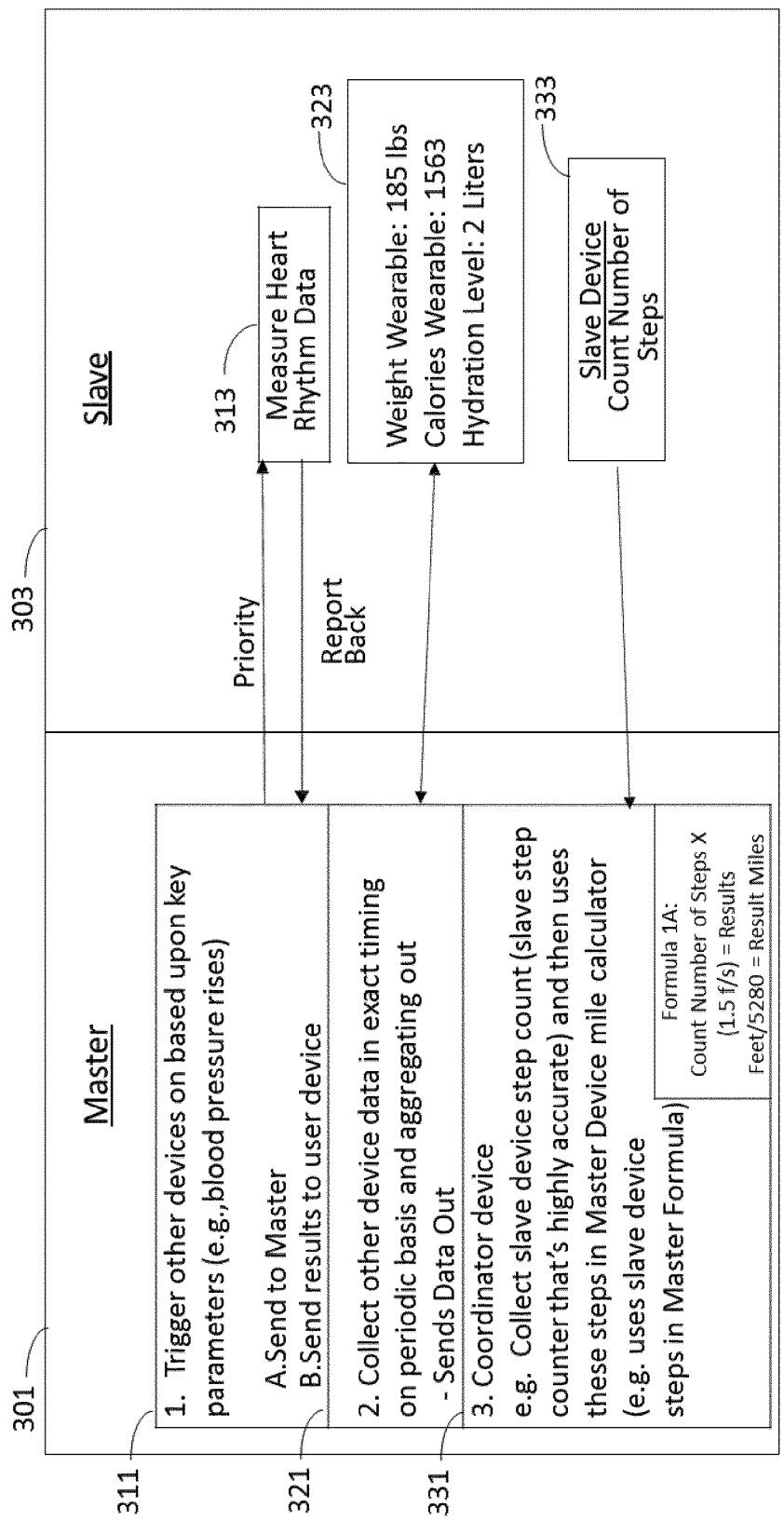
FIG. 3 illustrates exemplary assigned actions in a system for providing connecting relationships among wearable devices according to an embodiment of the present invention.

FIG. 3 illustrates exemplary assigned actions in a system for providing master-slave relationships among wearable devices. In FIG. 3, exemplary actions performed by the master device are illustrated under the "Master" heading 301, while exemplary actions performed by a slave device (or multiple slave devices in some embodiments) are illustrated under the "Slave" heading 303. References below to "the slave device 303" should be understood to refer to a slave device of a set of one or more exemplary slave devices. References below to "the master device 301" should be understood to refer to an exemplary device fulfilling a master role 201.

The master device 301 may trigger other (slave) devices based on the master device's measurement of one or more key parameters (e.g., rise in blood pressure in block 311). As such, the master may request that a slave device worn by the heart obtain another type of data (e.g., heart rhythm data) and report this data back to the master device (block 313). The master device 301 may, in some embodiments, request that the slave device 303 report a single recent measurement to the master device 301. In other embodiments, the master device 301 may request that the slave device 303 report multiple recent measurements to the master device 301. For example, master device 301 may send a priority request to the slave device 303 requesting heart rhythm data measured by the slave device 303 over the last three minutes preceding or subsequent to receipt of the request. The respective slave device 303 may report such data to the master device 301 (block 313), which may then use the data from the slave device 303 for an analysis.

In some embodiments, the master device 301 may trigger an alert or notification when it requests additional data from the slave device 303. For instance, the slave device 303 might vibrate, display text/graphics/video, play a sound, or release a small electric shock prior to measuring the user's health parameter (e.g., heart rhythm data in FIG. 3). Alternatively, the master device 301 could be the device that vibrates, displays text/graphics/video, plays a sound, or releases a small electric shock prior to the slave device measurement of the user's health parameter(s). Such alerts could be used, for example, to notify the user to place or rearrange the slave device to take a measurement properly, and thereby ensure that the slave device is secure or that the slave device is placed in the correct location on the user's body in order to make a proper measurement (e.g., to ensure that a respiratory monitor slave device is on the user's chest and not in another location). Such an alert could also be used to provide the user with a warning of a (still uncorroborated by the slave device) potential danger present in the measurement of the master device 301. Such an alert could also be used to indicate to the user that the user should perform a specific action or perform a visual check of a body part. For example, a user with Raynaud's disease could receive a vibration or alert at a slave device 303 or master device located at the user's wrist to let the user know to look at his/her hands and ensure that they have not turned white from poor blood circulation.

The master device 301 can, in some embodiments, just be a collector of information from all of the sensors located at the slave devices 303, so that information need not be collected individually from multiple different devices (block 321, block 323). In such cases, the master device 301 may be the assigned device for receiving reports (as in block 313), which the master device 301 may then report out to the user mobile device 241 or to the vendor/wearable network 233 (block 311). In some embodiments, the master device 301 may collect or aggregate data from slave devices 303 on a periodic basis (block 321).

Alternatively, the output of the slave device 303 may be used to improve the output of the master device 301. For example, a slave device 303 that acts as a step counter and is worn on the foot may provide the most accurate measurement of the number of steps taken by a user (block 333). The master device 301, however, may be worn on the wrist. In such instances, the master device 301 may act as a coordinating device that collects the step count from the slave device 303 and then uses that step count for a calculation based on the data from the slave device 303, such as by calculating a total distance using the number of steps reported by the slave device 303 (block 331). In some embodiments, the master device 301 may provide the most accurate measurement of another parameter (e.g., heart rate or location). In such embodiments, the master device 301 may also perform calculations based on a combination of sensor readings (e.g., calculating calories burned using both a heart rate measured by the master device 301 and a frequency of steps reported by the slave device 303). As such, highly accurate data from slave devices 303 may be provided to improve the accuracy of calculations performed by the master device 301.

In some embodiments, a master device 301 may be linked with multiple slave devices 303. In some embodiments, each slave device 303 does not know about the existence of the other slave devices 303. In other embodiments, one slave device 303 may know that another slave device 303 is also linked to the same master device 301. In such an embodiment, a first slave device 303 may "call" or "recommend" that the master device 301 obtain a further measurement from a second slave device 303, particularly when such measurements are helpful to examine in conjunction (e.g., heart rate and heart sound, or blood sugar level and insulin level). A master device 301 may then decide whether it wishes to follow this "call" or "recommendation" or not. Alternately, a master device 301 may decide alone that it should take measurements from multiple slave devices 303, or whether a measurement from a single slave device 303 will suffice.

Figure 4:
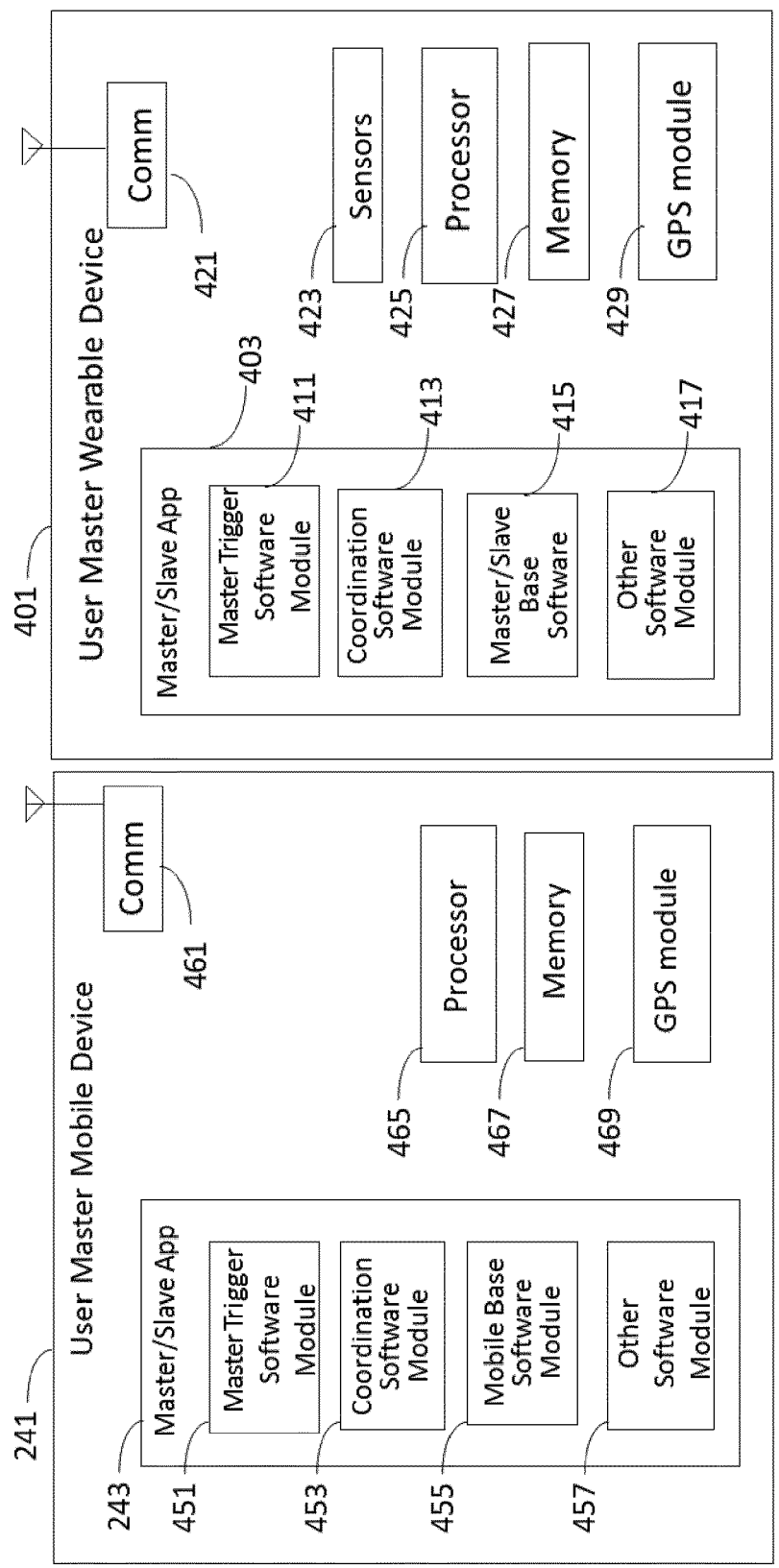
FIG. 4 illustrates an exemplary system for providing connecting relationships among wearable devices according to an embodiment of the present invention.

FIG. 4 illustrates an exemplary system including a user master mobile device 241 and a wearable device 401. The user master mobile device 241 may be, for example, a smartphone, a tablet, a laptop computer, a desktop computer, a gaming console, a smart television, a home entertainment system, a second wearable device, or another device. The user master mobile device 241 may, in some embodiments, include a communications module 461, a processor 465, a memory 467, and a global positioning system (GPS) module 469. The processor 465 can execute a master-slave software module application 243, which can includes master trigger software module 451, coordination software module 453, mobile base software module 455, and other software module 457.

The user master wearable device 401 may, in some embodiments, include a communications module 421, a processor 425, a memory 427, and a global positioning system (GPS) module 429. For example, the communications modules 421 and 461 can include transceivers to exchange data over a wireless channel. The processor 425 can execute a master-slave software module application 403, which can include master trigger software module 411, coordination software module 413, master/slave base software module 415 (i.e., base master software module 531, base slave software module 533, or both), and other software module 417. The user master wearable device 401 is shown as further including a sensors 423 including one or more sensors. The user master wearable device 401 may function as a master role 201 or a slave role. In some embodiments, the user master mobile device 241 and/or user master wearable device 401 may have additional modules not shown in FIG. 4. Similarly, in some embodiments, the user master mobile device 241 and/or user master wearable device 401 may be missing one or more modules shown in FIG. 4.

Figure 5:
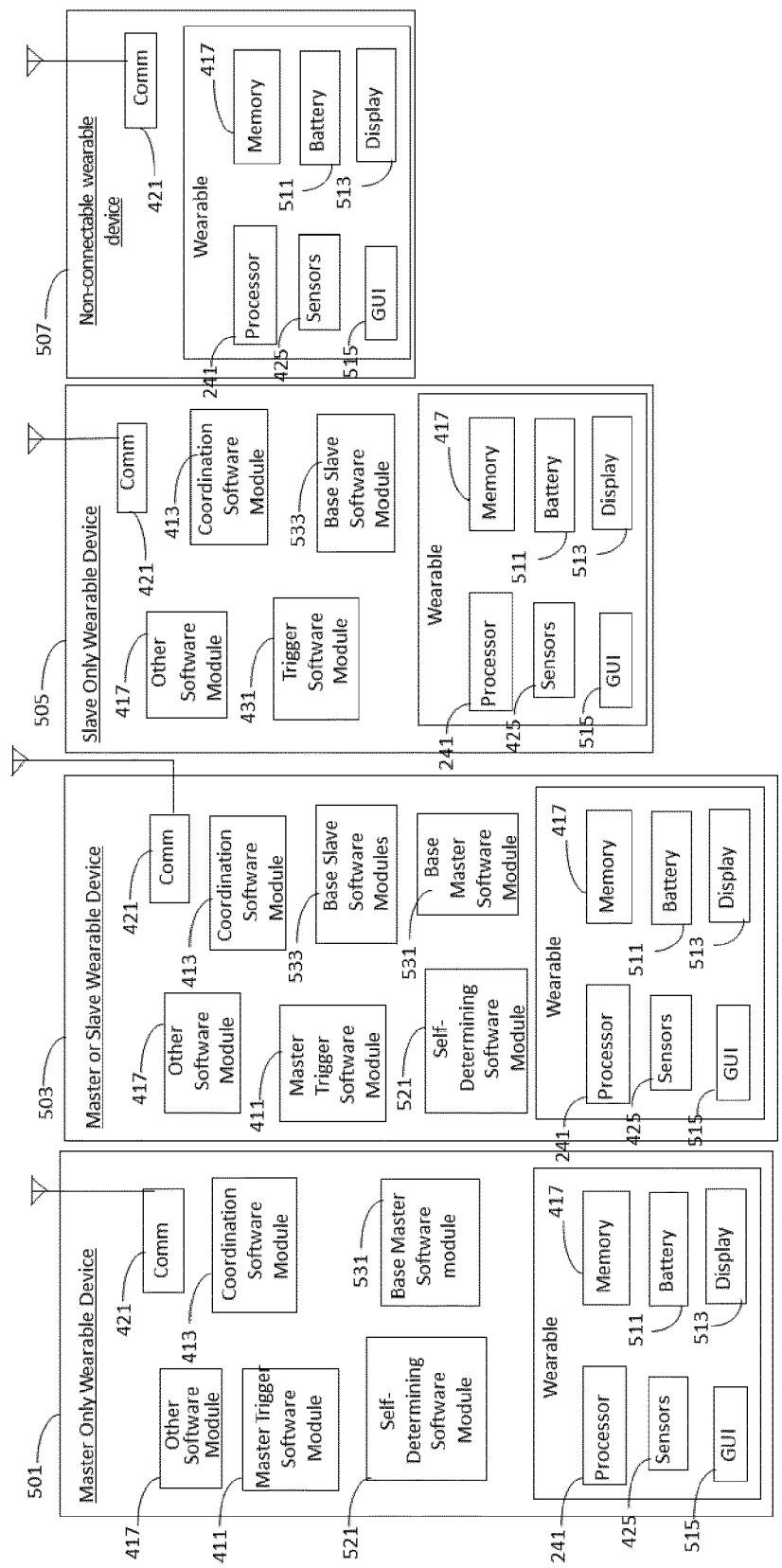
FIG. 5 illustrates an alternative system for providing connecting relationships among wearable devices according to an embodiment of the present invention.

FIG. 5 illustrates an alternative system for providing master-slave relationships among wearable devices. The illustrated system may include a variety of devices, each of which may or may not be capable of acting as a master device or a slave device. For example, this system may include a master-only wearable device 501, which is a wearable device that is only capable of acting in a master device role 201 and not in a slave device role. This system may also include a slave-only wearable device 505, which is a wearable device that is only capable of acting in a slave device role and not in a master device role 201. This system may also include a master-or-slave wearable device 503, which may act in either a master device role 201 or a slave device role depending on the circumstances. This system may also include a non-connectable wearable device 507 that is unable to act in either a master device role 201 or a slave device role.

As with the user master wearable device 401 in FIG. 4, the wearable devices (501, 503, 505, 507) of FIG. 5 may include a processor 425, sensors 423, a memory 427, a communications module 421, and a GPS module 429. The processor 425 of these wearable devices can execute a master/slave app 403 (not shown in FIG. 5) that can include master trigger software module 411, coordination software module 413, and other software module 417. The devices of FIG. 5 also may include a battery 511, a display 513, and a graphical user interface 515 to be shown on the display 513. It should be understood that the wearable devices of FIG. 4 and FIG. 5 show various exemplary embodiments, and any user master wearable device 401 may include any of the components shown in FIG. 4 or FIG. 5, or additional components not shown in either figure, and may further be missing components from either or both FIG. 4 and FIG. 5.

Devices capable of assuming a master device role 201, such as the master only wearable device 501 and the master or slave wearable device 503, may execute, with their processors 425, a base master software module 531, and a self-determining software module 521.

Devices capable of assuming a slave device role, such as the slave only wearable device 505 and the master or slave wearable device 503, may execute, with their processors 425, a base slave software module 533. Because the master or slave wearable device 503 can assume either a master device role 201 or a slave device role, it may include both a base master software module 531 and a base slave software module 533.

The self-determining software module 521 allows the user working with the master device to figure out which device is going to be the master and which device is going to be the slave. In some embodiments, the wearable devices capable of assuming a master device role 201—if there are multiple master-capable devices—can perform a handshake operation to exchange information and figure out which device should be the master. In some embodiments, even slave-only wearable devices can take part in such a handshake and can assist in figuring out which device should be the master. For example, the master may be the device with the greatest calculation capability or battery life spectrum. Alternately, if there is a single master-only device 501 as one of a group of devices, it can be chosen as for the master device role 201 so that more other devices can be used simultaneously.

The master trigger software module 411 allows for triggering of a priority request to be sent to a slave device. The coordination software module 413 provides real-time coordination of an input to a formula between the master 201 and the slave. For example, a step count provided by the slave may be used by the master to improve its accuracy.

Base slave software module 532 allows a slave device to run and operate as a slave. As a slave, general responsibilities may be limited to sensing its particular parameter(s) with its sensor(s) 423 and reporting out such information to the master device role 201. A master generally has to do more.

As such, a device may execute its self-determining software module 521 to determine whether it is currently acting as master 201 or slave. If the device is determined to be a master 201, the base master software module 531 may be executed, as well as the master trigger software module 411 and the coordination software module 413. Base slave software module 533 (if present) is not executed on a device assigned to be a master device 201. Conversely, a slave device lacks the base master software module 531 and only has the master trigger software module 411, coordination software module 413, and base slave software module 533. Some devices may not be able to be connected (i.e., non-connectable wearable device 507), thereby being unable to serve as either master or slave and lacking the software module specific to each role.

Figure 6:
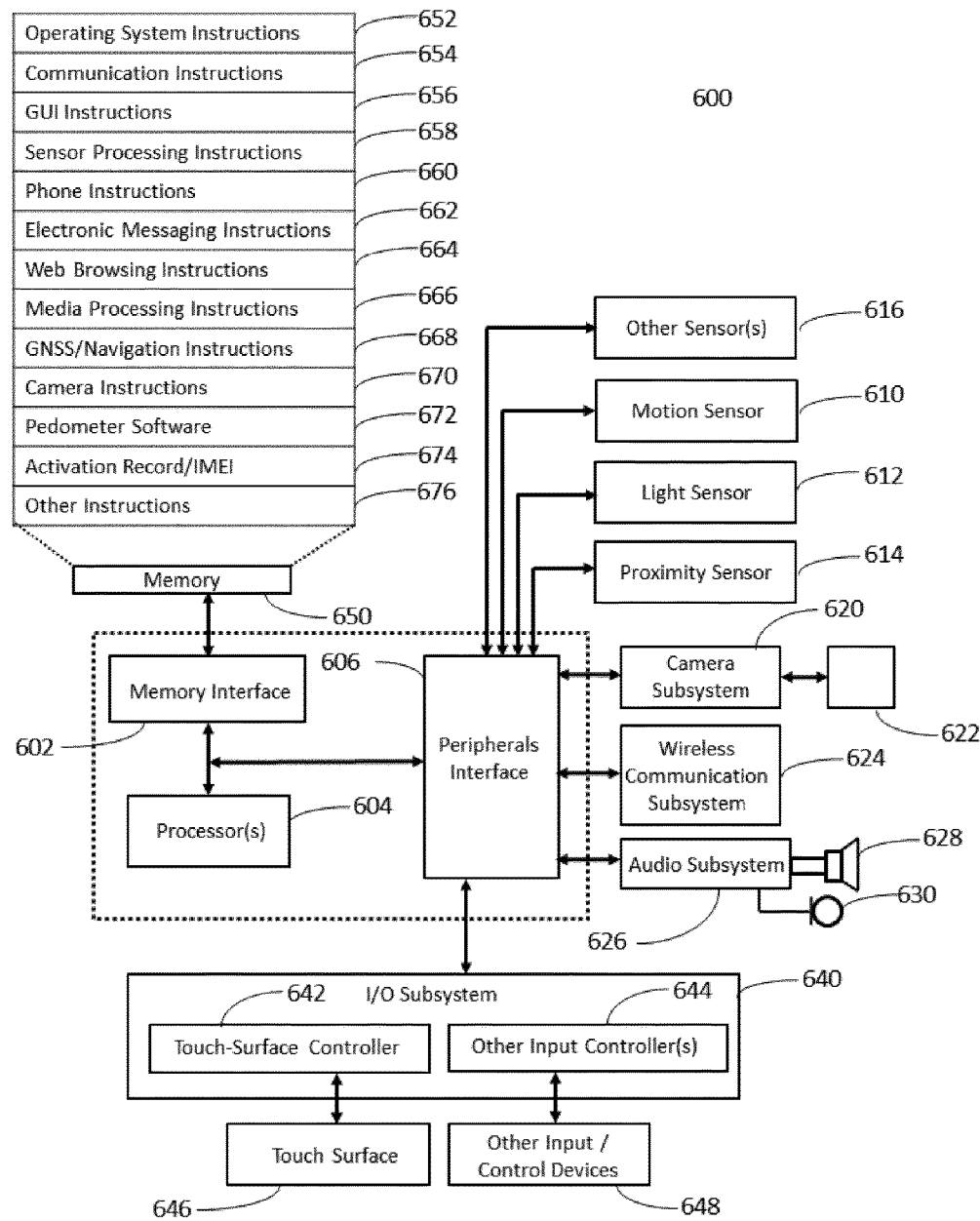
FIG. 6 shows a block diagram of an exemplary computing device that can implement the features and processes described herein according to an embodiment of the present invention.

FIG. 6 illustrates a mobile device architecture that may be utilized to implement the various features and processes described herein. Architecture 600 can be implemented in any number of portable devices including but not limited to smart devices, including smart wearable devices. Architecture 600 as illustrated in FIG. 6 includes a memory interface 602, a processors 604, and a peripheral interface 606. The memory interface 602, the processors 604 and the peripherals interface 606 can be separate components or can be integrated as a part of one or more integrated circuits. The various components can be coupled by one or more communication buses or signal lines.

Processors 604 as illustrated in FIG. 6 are meant to be inclusive of data processors, image processors, central processing unit, or any variety of multi-core processing devices. Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be exemplified in the context of an accelerometer or gyroscope, could be utilized to detect movement and orientation of the mobile device. Display objects or media could then be presented according to a detected orientation (e.g., portrait or landscape).

Other sensors 616 could be coupled to peripherals interface 606, such as a temperature sensor, a biometric sensor, or other sensing devices to facilitate corresponding functionalities. Other sensors 616 may include a location processor (e.g., a global positioning transceiver) coupled to peripherals interface 606 to allow for generation of geo-location data thereby facilitating geo-positioning. Other sensors 616 may additionally or alternatively include an electronic magnetometer connected to peripherals interface 606 to provide data related to the direction of true magnetic North whereby the mobile device could enjoy compass or directional functionality. Camera subsystem 620 and an optical sensor 622 such as a charged coupled device (CCD) or a complementary metal-oxide semiconductor (CMOS) optical sensor can facilitate camera functions such as recording photographs and video clips.

Communication functionality can be facilitated through one or more communication subsystems 624, which may include one or more wireless communication subsystems. Wireless communication subsystems 624 can include 802.5 or Bluetooth transceivers as well as optical transceivers such as infrared. Wired communication system can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.5 communication networks, code division multiple access (CDMA) networks, or Bluetooth networks. Communication subsystem 624 may include hosting protocols such that the device may be configured as a base station for other wireless devices. Communication subsystems can also allow the device to synchronize with a host device using one or more protocols such as TCP/IP, HTTP, or UDP.

Audio subsystem 626 can be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 can be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 can display virtual or soft buttons and a virtual keyboard, which can be used as an input/output device by the user.

Other input controllers 644 can be coupled to other input/control devices 648 such as one or more buttons, rocker switches, thumb-wheels, infrared ports, USB ports, and/or a pointer device such as a stylus. The one or more buttons (not shown) can include an up/down button for volume control of speaker 628 and/or microphone 630. In some implementations, device 600 can include the functionality of an audio and/or video playback or recording device and may include a pin connector for tethering to other devices.

Memory interface 602 can be coupled to memory 650. Memory 650 can include high-speed random access memory or non-volatile memory such as magnetic disk storage devices, optical storage devices, or flash memory. Memory 650 can store operating system 652, such as Darwin, RTXC, LINUX, UNIX, OS X, ANDROID, WINDOWS, or an embedded operating system such as VXWorks. Operating system 652 may include instructions for handling basic system services and for performing hardware dependent tasks. In some implementations, operating system 652 can include a kernel.

Memory 650 may also store communication instructions 654 to facilitate communicating with other mobile computing devices or servers. Communication instructions 654 can also be used to select an operational mode or communication medium for use by the device based on a geographic location, which could be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; pedometer software 672 to facilitate pedometer-related processes; activation record/IMEI software 674 to facilitate activation record/IMEI-related processes; and other instructions 676 for any other application that may be operating on or in conjunction with the mobile computing device. Memory 650 may also store other software instructions for facilitating other processes, features and applications, such as applications related to navigation, social networking, location-based services or map displays.

Various embodiments described herein achieve various functionality through the execution of instructions by a processor. It will be understood that, while various examples are described in the context of instructions actively performing steps or other actions, any such actions will actually be performed by the processor that executes such instructions.

Note that the master/slave app (243, 403), the master trigger software module (411, 451), the coordination software module (413, 453), the mobile base software module 455, the master/slave base software module 415, the other software module (417, 457), the self-determining software module 521, the base master software module 531, the base slave software module 511, pedometer software 672, and activation record/IMEI software 674 are softwares that are stored in one of the memory for execution by the processor.

The memory 650 may store operating system instructions 652, communication instructions 654, GUI instructions 656, sensor processing instructions 658, phone instructions 660, electronic messaging instructions 662, web browsing instructions 664, media processing instructions 666, GNSS/navigation instruction 668, camera instructions 670, and other instructions 676 for execution by the processor 604. It will be understood that these instructions may be alternatively or additionally stored in a non-volatile storage device such as the storage device storing the reference link database or another storage device (not shown). For example, the instructions may be stored in a flash memory or an electronic read only memory (ROM) until they are to be executed by the processor, at which point they are copied to the memory 650. As used herein, the term storage will be understood to refer to non-volatile memories.

The processor 604 may be virtually any device capable of performing the functions described herein including the functions described above in connection with the operating system instructions 652, communication instructions 654, GUI instructions 656, sensor processing instructions 658, phone instructions 660, electronic messaging instructions 662, web browsing instructions 664, media processing instructions 666, GNSS/navigation instruction 668, camera instructions 670, and other instructions 676. For example, the processor 604 may include one or more microprocessors, one or more field-programmable gate arrays (FPGA), or one or more application-specific integrated circuits (ASIC). In some embodiments, the processor may not utilize stored instructions to perform some or all of the functions described herein; for example, an ASIC may be hardwired to perform one or more of the functions describe above with reference to the operating system instructions 652, communication instructions 654, GUI instructions 656, sensor processing instructions 658, phone instructions 660, electronic messaging instructions 662, web browsing instructions 664, media processing instructions 666, GNSS/navigation instruction 668, camera instructions 670, and other instructions 676. In some such embodiments, the operating system instructions 652, communication instructions 654, GUI instructions 656, sensor processing instructions 658, phone instructions 660, electronic messaging instructions 662, web browsing instructions 664, media processing instructions 666, GNSS/navigation instruction 668, camera instructions 670, and other instructions 676 may be omitted because they are already embodied in the processor 604 without the need for stored instructions.

Each of the above identified instructions and applications can correspond to a set of instructions for performing one or more functions described above. These instructions need not be implemented as separate software programs, procedures, or modules. Memory 650 can include additional or fewer instructions. Furthermore, various functions of the mobile device may be implemented in hardware and/or in software, including in one or more signal processing and/or application specific integrated circuits.

Certain features may be implemented in a computer system that includes a back-end component, such as a data server, that includes a middleware component, such as an application server or an Internet server, or that includes a front-end component, such as a client computer having a graphical user interface or an Internet browser, or any combination of the foregoing. The components of the system can be connected by any form or medium of digital data communication such as a communication network. Some examples of communication networks include LAN, WAN and the computers and networks forming the Internet. The computer system can include clients and servers. A client and server are generally remote from each other and typically interact through a network. The relationship of client and server arises by virtue of computer programs running on the respective computers and having a client-server relationship to each other.

One or more features or steps of the disclosed embodiments may be implemented using an Application Programming Interface (API) that can define on or more parameters that are passed between a calling application and other software code such as an operating system, library routine, function that provides a service, that provides data, or that performs an operation or a computation. The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer may employ to access functions supporting the API. In some implementations, an API call can report to an application the capabilities of a device running the application, such as input capability, output capability, processing capability, power capability, and communications capability.

Figure 7:
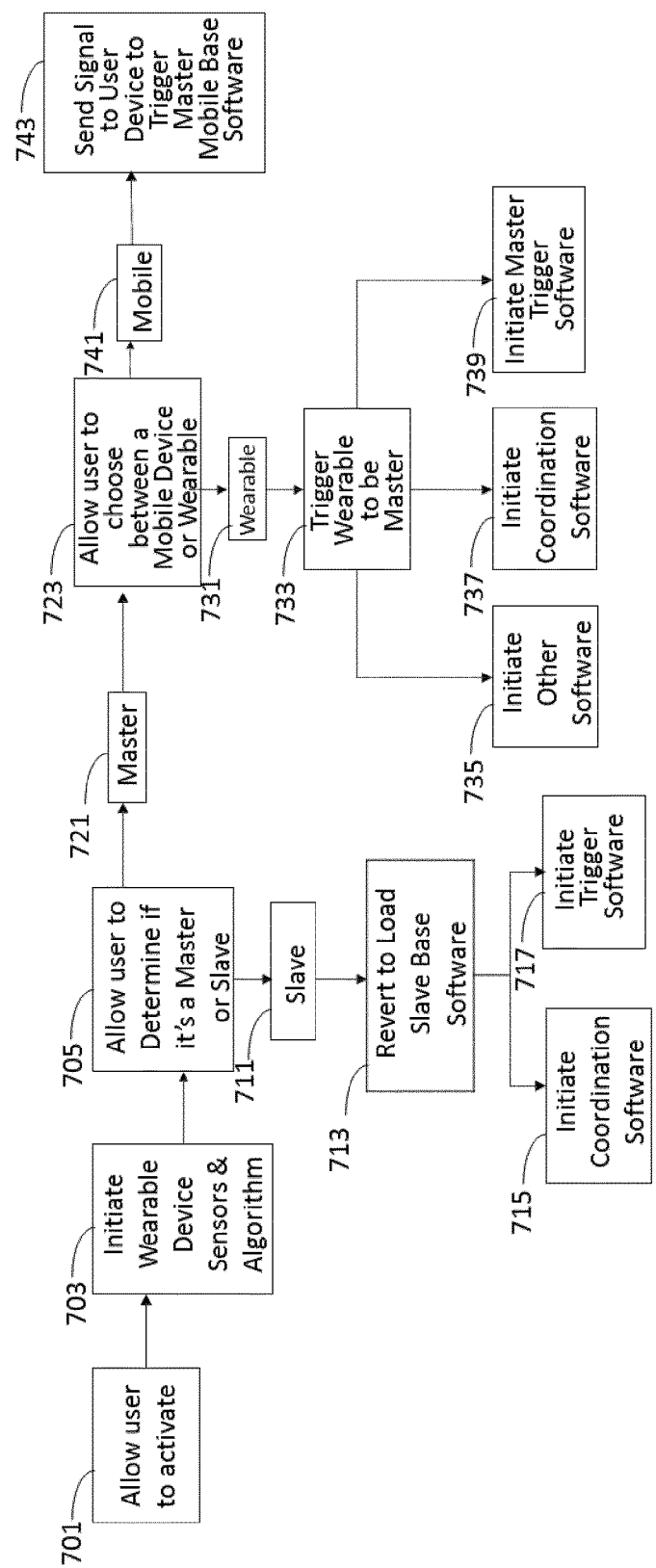
FIG. 7 shows a flowchart illustrating an exemplary master base software module method for providing connecting relationships among wearable devices according to an embodiment of the present invention.

FIG. 7 is a flowchart illustrating an exemplary master device base software method for providing master-slave relationships among wearable devices. The user may activate a user master wearable device 401 (block 701). The user master wearable device 401 and sensors algorithms may thereby be initiated (block 703). The user may thereafter determine if the user master wearable device 401 is going to be a master 201 or slave (block 705). If the user master wearable device 401 is going to be a master 201 (block 721), the user may further choose between whether the master 201 is the user master mobile device 241 or the user master wearable device 401 (block 723). If the master 201 is going to be the user master mobile device 241 (block 741), a signal may be sent to the user master mobile device 241 to trigger its master base software module (block 743). If the master 201 is going to be the user master wearable device 401 (block 731), a signal may be sent to the user master wearable device 401 to trigger its master trigger software module (block 733), which may initiate the coordination software module (block 737), master base software module (block 739), and other software module (block 735).

If the user selects slave at block 705 (block 711), the base slave software module may therefore be loaded (block 713) to initiate its respective trigger software module (431) (block 717) and coordination software module (block 715). In this way, self-determination may be based on user preference or selection, but may also be performed automatically.

While the flow diagram in FIG. 7 shows a particular order of operations performed by certain embodiments of the invention, it should be understood that such order is exemplary (e.g., alternative embodiments can perform the operations in a different order, combine certain operations, overlap certain operations, etc.).

Figure 8:
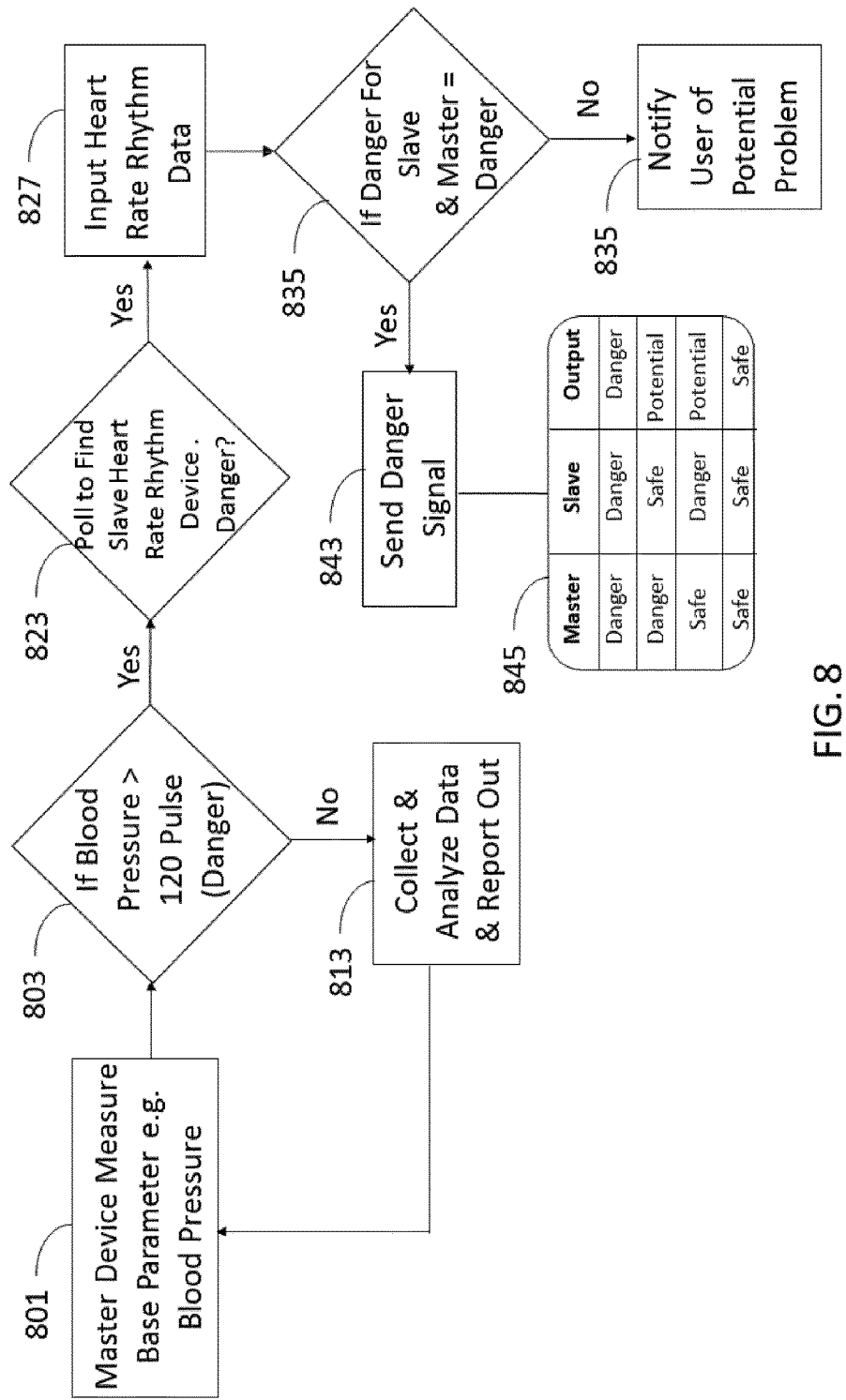
FIG. 8 shows a flowchart illustrating an exemplary master trigger method for providing connecting relationships among wearable devices according to an embodiment of the present invention.

FIG. 8 is a flowchart illustrating an exemplary master trigger method for providing master-slave relationships among wearable devices. Such a trigger method may allow for the master device to measure a base parameter (e.g., blood pressure) (block 801). If the master device's parameter is determined to not be in a risky or dangerous range (e.g., blood pressure safely below 120 mm Hg in block 803), the master device may collect the sensor data, analyze it if necessary, and report the data out (e.g., to the user mobile device 241 or vendor/wearable network 233) (block 813).

If the master device's parameter is determined to be in a risky or dangerous range (e.g., blood pressure detected over 120 mm Hg in block 803), the master may then poll slave devices (e.g., for heart rate rhythm in block 823). If the data from the slave device (e.g., heart rate rhythm) is also in a dangerous range (e.g., measurable heart arrhythmia), the data from the slave device may be input back to the master device (block 827), where the master device can determine whether the data from the slave device is within the dangerous range (block 831).

If the data from the slave device is not in a dangerous range but the data from the master device is in a dangerous range, then the master device may notify the user of the master device of a potential health problem (block 835).

If the data from the slave device is in a dangerous range and the data from the master device is also in a dangerous range, then the master device may warn the user of the master device of a that the user is currently in danger, or at least has a heightened probability of danger (block 843), since the initial potential sign of danger has been confirmed.

A table of different results between master-slave may be used to determine whether danger (or potential danger) exists or not (block 845). According to this table, the user may be sent a notification regarding the potential or detected danger.

While the flow diagram in FIG. 8 shows a particular order of operations performed by certain embodiments of the invention, it should be understood that such order is exemplary (e.g., alternative embodiments can perform the operations in a different order, combine certain operations, overlap certain operations, etc.).

FIG. 9A illustrates an implementation of an exemplary coordination method for providing master-slave relationships among wearable devices. Such coordination may occur, for example, with respect to measuring calories for users varying in gender, age, and current weight (see exemplary results 911). Such statistics may be entered ahead of time, thereby providing data that can be used in formulae (e.g., factors or ratios in the exemplary formulae provided). An original formula might use a number of steps (e.g., a number of steps times 1.5 feet per second and then divided by 5280 to convert to miles) (block 901).

Coordination, however, may be used to generate a real-time step count. The master running master coordination software module may therefore request that the slave (e.g., pedometer worn on an ankle) running slave coordination software module provide an accurate step count (block 903). Based on the response, the parameter (i.e., step count) may be updated (block 905), thereby providing a modified formula with real-time, accurate measurements (block 907).

FIG. 9B is a flowchart illustrating an exemplary coordination method for providing master-slave relationships among wearable devices. In one embodiment, this begins with a user initiating a master device 201 (block 951). The user then inputs a base parameter (block 953). The master device 201 then searches for a slave wearable device (e.g., a step counter wearable device in block 955). If the master device 201 does not locate a slave wearable device or cannot connect to it, then in block 959, the master device 201 can continue to use its original calculation formula (e.g., formula in block 901). However, if the master device 201 does locate a slave device, then it can instruct that slave device to take measurements (block 963), instruct that slave device to sync the measurements (block 965), and ultimately download the measurements from the slave device in real-time (block 967). After this, the master device 201 can modify its formula in some embodiments, as shown in block 907.

While the flow diagrams in FIG. 9A and FIG. 9B show a particular order of operations performed by certain embodiments of the invention, it should be understood that such order is exemplary (e.g., alternative embodiments can perform the operations in a different order, combine certain operations, overlap certain operations, etc.).

Figure 10:
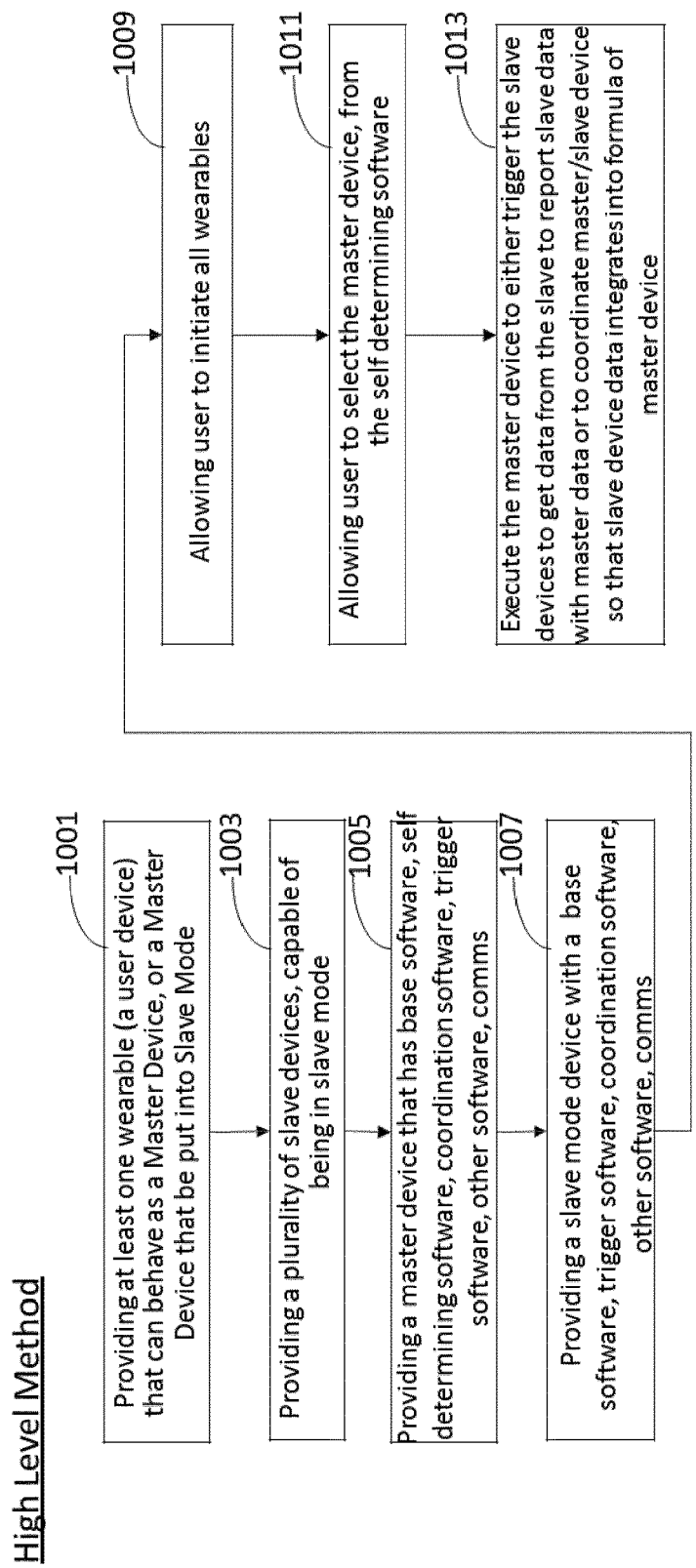
FIG. 10 shows a flowchart illustrating an exemplary method for providing connecting relationships among wearable devices according to an embodiment of the present invention.

FIG. 10 is a flowchart illustrating an exemplary method for providing master-slave relationships among wearable devices. A wearable device capable of acting as master may be provided (block 1001), along with slave—capable devices (block 1003). The master may be provided with base software module, self-determining software module, coordination software module, trigger software module, other software module, and a communication module/interface (block 1005). Likewise, the slave-capable devices may be provided with slave base software module, trigger software module, coordination software module, other software module, and a communications module/interface (block 1007).

The user may initiate all wearable devices (block 1009) and select the master device from the self-determining software module (block 1011). The master thereafter may trigger the slave devices, request data from the slaves, thereby coordinating or integrating such data with the operations of a master device (block 1013).

Figure 11:
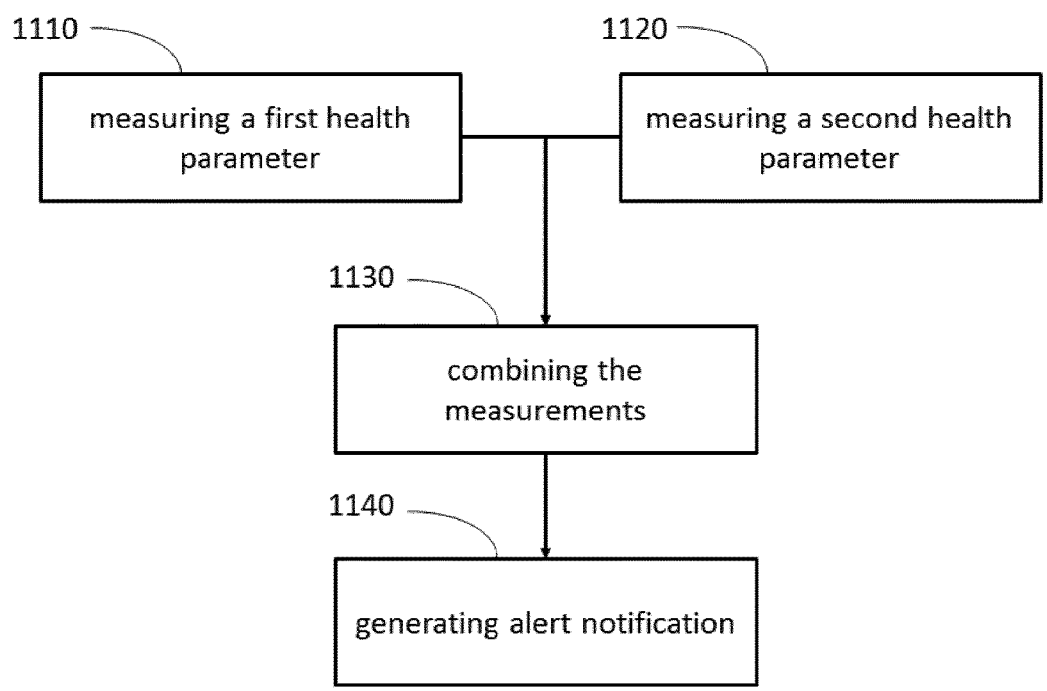
FIG. 11 shows a block diagram of a computer-implemented method for providing connecting relationships between wearable devices according to one embodiment of the invention.

FIG. 11 shows a block diagram of a computer-implemented method for providing connecting relationships between wearable devices according to one embodiment of the invention. The method includes measuring a first health parameter of a user via one or more sensors of a first wearable device 1110 and measuring a second health parameter of the user via one or more sensors of a second wearable device 1120. The method also includes determining an alert action based on a combination of the measurements of the first and the second health parameter 1130 and generating a notification to the user based on the alert action 1140. In such a manner, multiple health parameters of the users determined by different sensors can be used to better assess the health condition of the user. For example, the method can use measurements of blood pressure and a heart rate to determine more accurate alert action that, e.g., the alert action determined only based on the blood pressure parameters.

In different implementations of the embodiment, the first or the second wearable device can act as a master device to perform the comparison. Alternatively, the master role can be delegated to a third device, such as a smartphone.

Figure 12A:
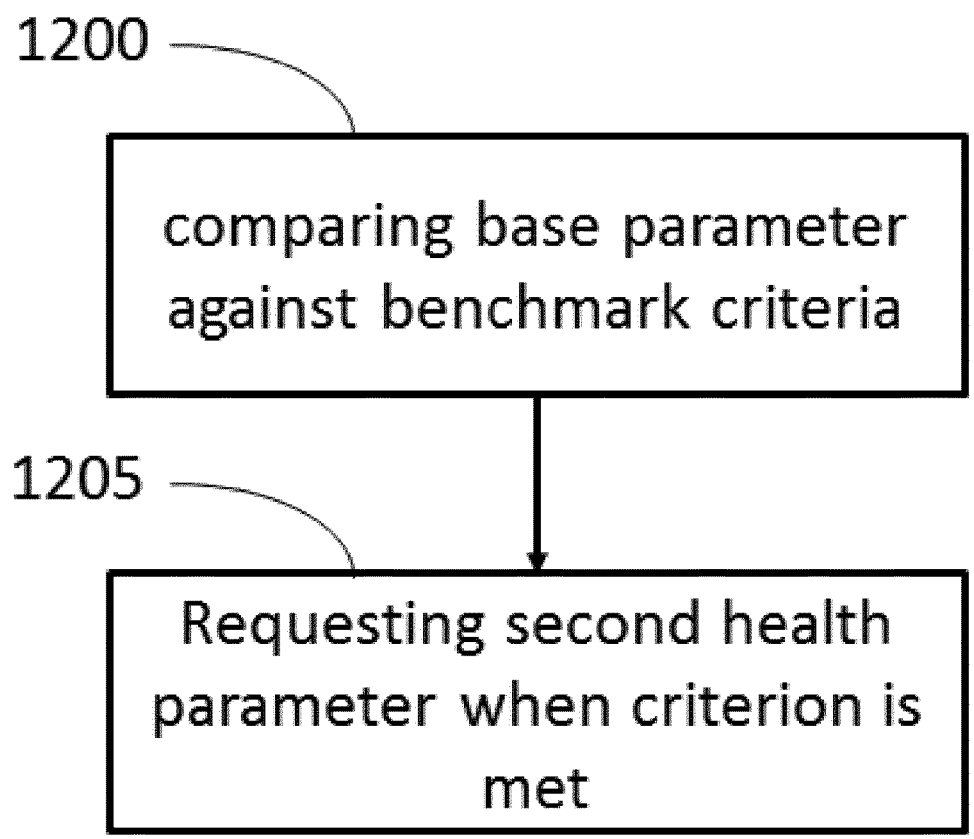
FIGS. 12A and 12B show block diagrams of methods according to different embodiments where the wearable devices assigned to master-slave roles.

FIG. 12A shows a block diagram of a method according to one embodiment, wherein the determination of the alert action is performed by the first wearable device assigned to a master role. In this embodiment, the first health parameter is a base parameter for monitoring the health of the user. Steps of the method can be performed by a processor of the first wearable device.

The method includes comparing the measurement of the base parameter against benchmark criteria 1200 and requesting the measurement of the second health parameter from the second wearable device assigned to a slave role, when the base parameter meets a certain predetermined criterion 1205. Examples of criteria for comparison include, but not limited to, sudden changes in the measurements of the base parameters, detection of the potential dangerous condition of the user, reduction of the quality of the received measurements, e.g., due to the lack of energy in the wearable device.

Figure 12B:
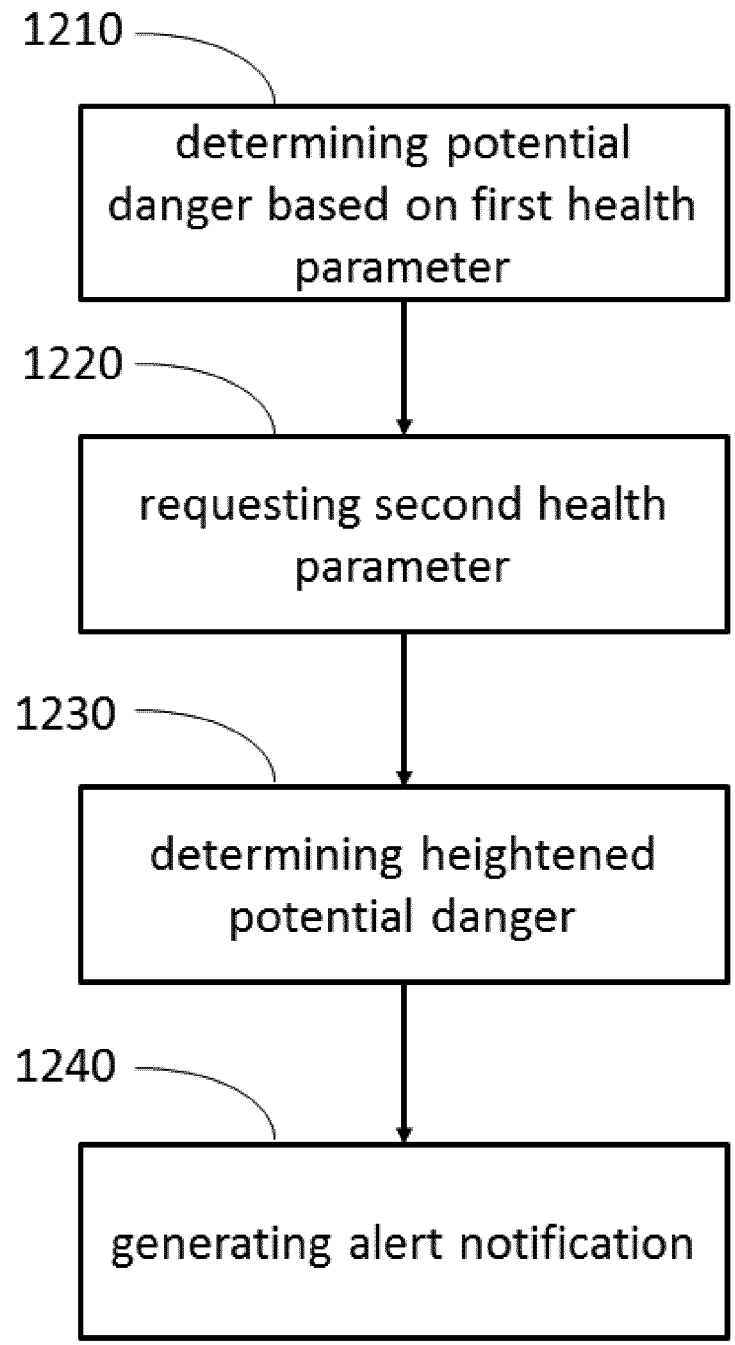

FIG. 12B shows a block diagram of a method according to another embodiment that determines the existence of the potential danger to the user. The method includes determining whether the measurement of the base parameter indicates a potential danger for the user 1210 and requesting the measurement of the second health parameter from the second wearable device assigned to a slave role 1220. The method further includes determining whether the alert action indicates that a heightened potential danger exists 1230 and generating the notification based on the determination of the existence of the heightened potential danger 1240. This embodiment allows comparing the measurements from different wearable device only when the danger for the user exists. In addition, one implementation the method includes alerting the user prior to requesting the measurement of the second health parameter.

Some embodiments of the invention are based on recognition that the same health parameter can be measured by sensors of different wearable devices. For example, the health parameter for a number of steps can be measured by a step counting sensor in a wrist bracelet that uses a swing motion of the arm of the user, as well by a step counting sensor that uses GPS signal. In some situations, one of the sensors may not be available or not suitable for accurate measurement of the health parameter. For example, the GPS can be used to determine the number of steps of the user running outdoors, but is less helpful when the user is indoor on a treadmill.

Figure 13:
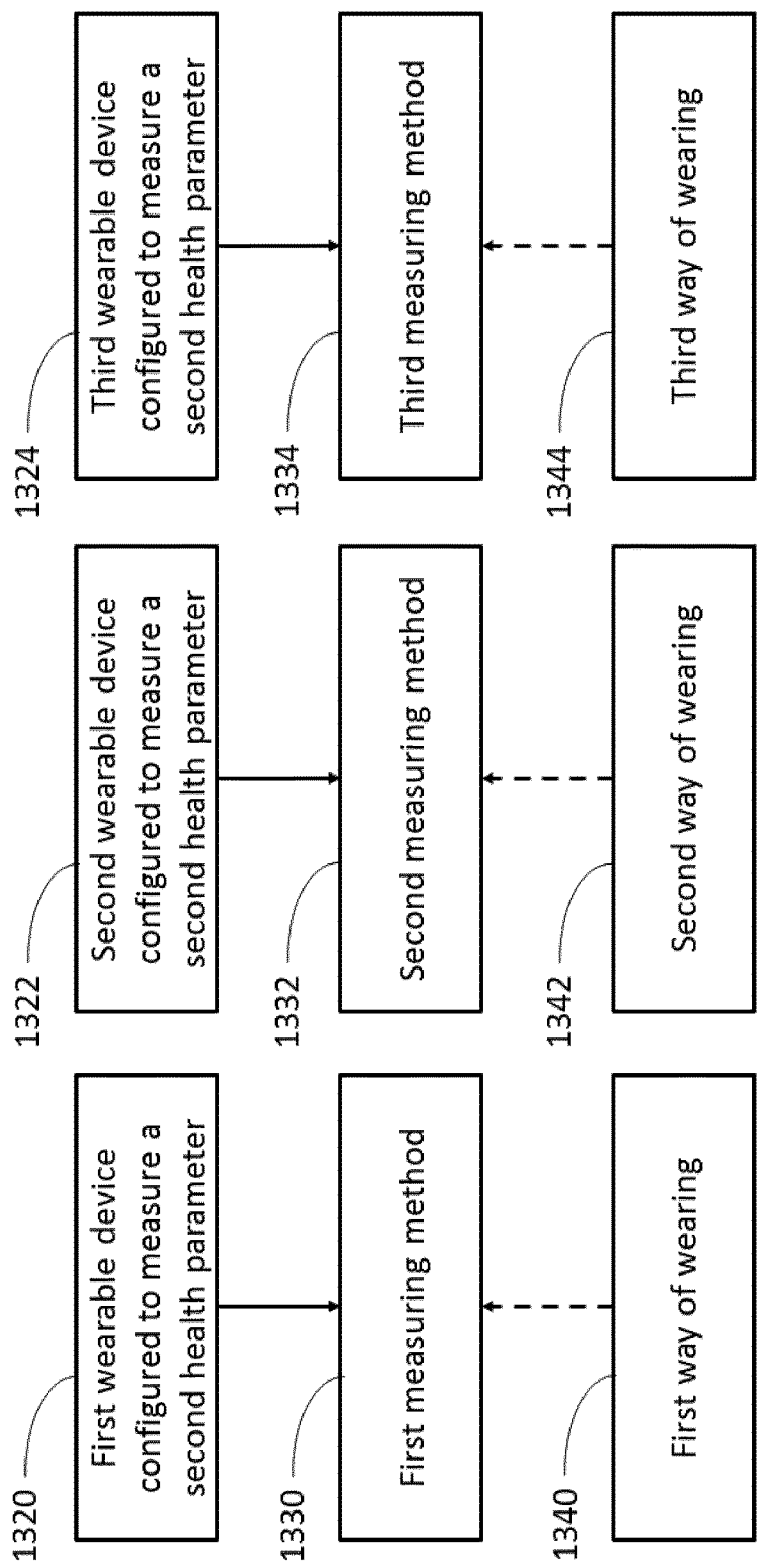
FIG. 13 shows three devices that may be selected for configuring to measure the same health parameter of a user according to some embodiments of the invention.

FIG. 13 shows three devices that may be selected for configuring to measure the same health parameter of a user. For the sake of this example, the health parameter is the number of steps traveled by the user, and the devices include a first wearable device 1320 (i.e., wrist bracelet) having an accelerometer, a second wearable device 1322 (i.e., pedometer) attached to a foot of the user, and a third wearable device 1324 (i.e., location sensor) embedded in a footwear of the user. All of those devices are configured to count the steps of the user using different measuring methods. For example, the first measuring method 1330 uses an acceleration of the user to measure steps, the second measuring method 1332 uses the swing of the user foot, and the third measuring method 1334 uses the changes on the GPS location of the user to estimate a number of steps required for such a change.

According to some embodiments of the invention, the wearable device assigned to a master role can select from available wearing methods the wearing method that is optimal for a specific health parameter. As used herein, the optimal measuring method and/or the optimal wearable device for measuring the health parameter are better suited for measuring the health parameter than the other methods available to the master device. For example, in the above-mentioned example, the measuring method of the pedometer can be selected to measure the number of steps over the other available methods. In another example and/or for measuring another health parameter, other measuring methods can be selected.

In some situations, the method uses the ways of wearing the wearable device 1340, 1342, and 1344 for selecting the optimal measuring method. For example, the pedometer attached to the foot of the user is more accurate than the pedometer attached to the arm. The master device can store in a memory a lookup table matching different health parameters with different measuring methods and/or ways of wearing the wearable device. In some embodiments, the lookup table is ordered, so the master device can select 1310 the optimal measuring method from the measuring methods available to the user.

Figure 14A:
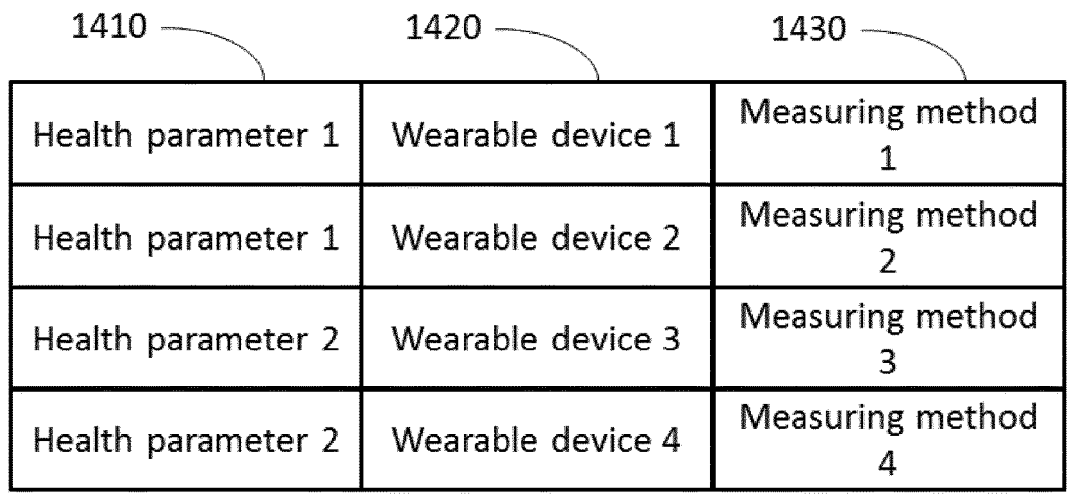
FIGS. 14A and 14B show diagrams of lookup tables used by some embodiments to select a wearable device for measuring the health parameter.
Figure 14B:
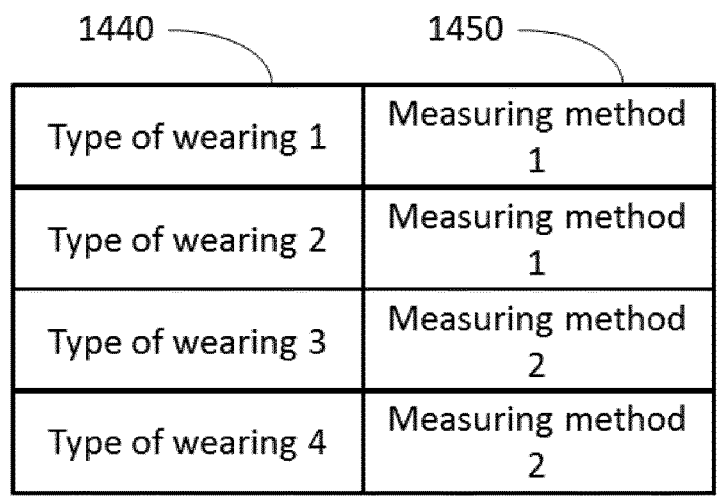

FIGS. 14A and 14B show diagrams of lookup tables used by some embodiments to select a wearable device for measuring the health parameter. The lookup table can associate a list of health parameters 1410 with different ways of the wearable devices 1420 and corresponding measuring methods 1430. Using this lookup table, the master device can test if the available wearable devices can measure the needed health parameter and select the optimal wearable device from a set of available wearable devices. For example, in FIG. 15A, two wearable devices are configured to measure health parameter 1. If the user is wearing both wearable devices, the master can select the first wearable device from top of the list.

FIG. 14B shows an example of lookup table associating the measuring methods 1440 with the ways of wearing the wearable devices 1450. For example, if multiple measuring methods are equally optimal for measuring the health parameter, the master device can test the way of wearing of the wearable devices to select the most optimal one.

Figure 15:
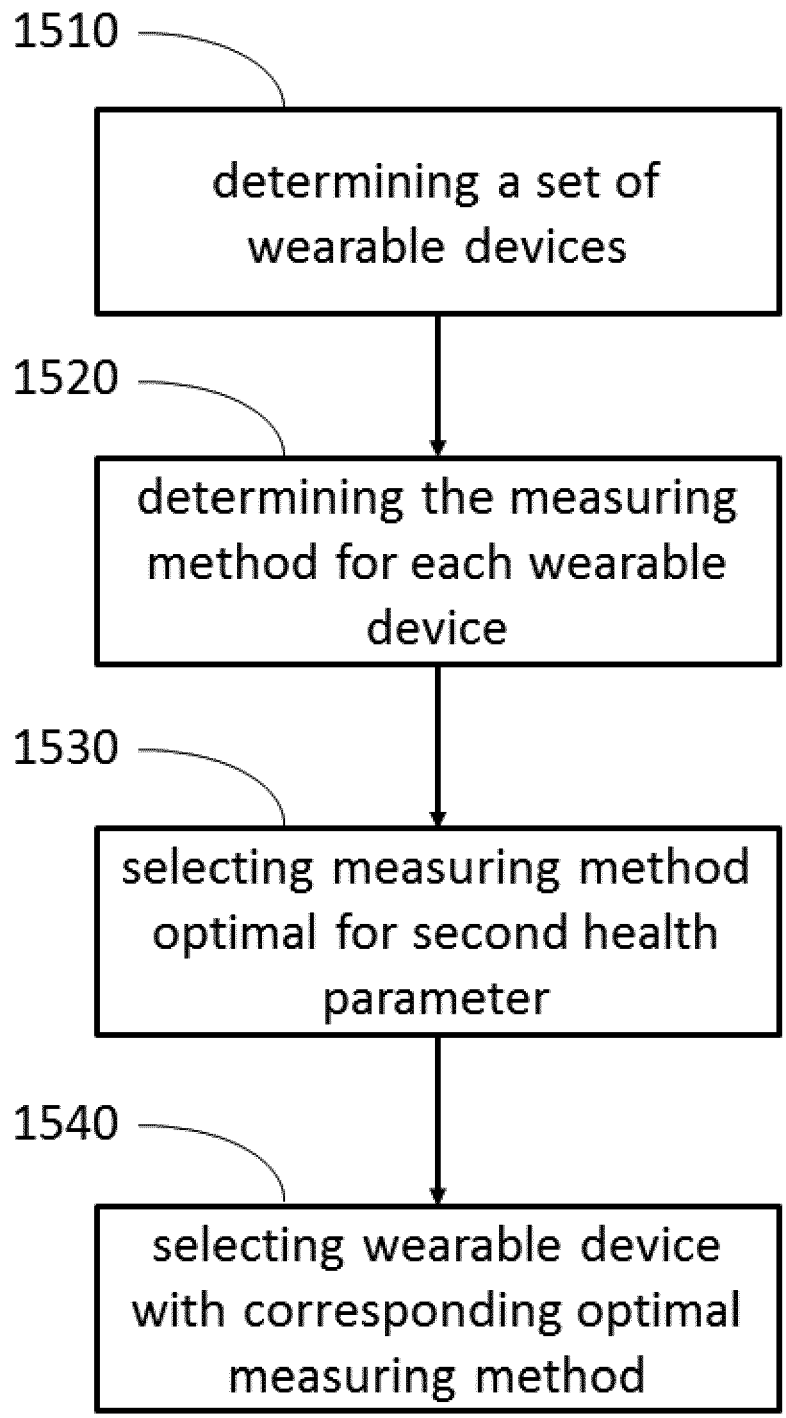
FIG. 15 shows a block diagram of a method for selecting the second wearable device to work cooperatively with the first wearable device according to one embodiment of the invention.

FIG. 15 shows a block diagram of a method for selecting the second wearable device to work cooperatively with the first wearable device. The method includes determining a set of wearable devices that the user is wearing, wherein each wearable device in the set is configured to measure the second health parameter using a corresponding measuring method 1510 and determining the measuring method for each wearable device in the set to produce a set of measuring methods 1520. The method also includes selecting, from the set of measuring methods, the measuring method optimal for measuring the second health parameter 1530 and selecting the wearable device with corresponding optimal measuring method as the second wearable devices having the slave role for measuring the second health parameter 1540.

In some implementations, the optimal measuring method is determined based on a way of wearing of the corresponding wearable device. For example, one embodiment determines at least two measurements of the second health parameter using at least two wearable devices having different ways of wearing. Examples of the ways of wearing include armwear, eyewear, footwear and wearable devices embedded into the close of the user. This embodiment is based on recognition that some ways of wearing are more advantageous for some types of health parameters.

Additionally or alternatively, some embodiments select the measurement of the second health parameter based on a function of the at least two measurements of the second health parameter. For example, the function can be a weighted average of the measurements of the second health parameter measured by the sensors of the first and the second wearable devices or by sensors having the slave role for measuring the second health parameter. For example, the method can average the number of steps determined by the devices 1330, 1332, and 1334.

In some embodiments, the weight is equal for all or some measurements. In those situations the weighted function determines the mathematical average. However, in alternative embodiments, the weight of the weighted average can be different for different measurements to adapt the function to the different situations. For example, the weight can be updated in response to detecting a change in an activity of the user or can use a greater weight for measurements of the pedometer versus the measurements of the accelerator.

While diagrams used herein figure show a particular order of operations performed by certain embodiments of the invention, it should be understood that such order is exemplary (e.g., alternative embodiments can perform the operations in a different order, combine certain operations, overlap certain operations, etc.).

Embodiments of the invention also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures can be performed by processing logic that comprises hardware (e.g. circuitry, dedicated logic, etc.), software module (e.g., embodied on a non-transitory computer readable medium), or a combination of both. Although the processes or methods are described above in terms of some sequential operations, it should be appreciated that some of the operations described can be performed in a different order. Moreover, some operations can be performed in parallel rather than sequentially.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

The invention claimed is:

1. A computer-implemented method for providing connecting relationships between wearable devices, the method comprising:
    measuring a base vital sign of a user via one or more sensors of a first wearable device;
    determining whether or not the base vital sign meets a certain predetermined threshold criterion;
    in response to the base vital sign meeting the certain predetermined threshold criterion, requesting measurement of a second vital sign of the user via one or more sensors of a second wearable device;
    determining an alert action based on a combination of the base vital sign and the second vital sign; and
    generating a notification to the user based on the alert action.

2. The method of claim 1, wherein the alert action is determined by
    a smartphone, and wherein the first and the second wearable devices have different ways of being worn.

3. The method of claim 1, wherein the first wearable device receives measurements of vital signs of the user from a plurality of wearable devices.

4. The method of claim 1, further comprising:
    alerting the user prior to requesting the measurement of the second vital sign.

5. The method of claim 1, further comprising:
    additionally measuring the second vital sign by the sensor of the first wearable device; and
    selecting the measurement of the second vital sign for comparing with the base vital sign based on a function of the measurements of the second vital sign measured by the sensors of the first and the second wearable devices.

6. The method of claim 5, further comprising:
    detecting a change in an activity of the user; and
    updating the function in response to the detecting the change.

7. The method of claim 6, wherein the function determines a weighted average of the measurements of the second vital sign measured by the sensors of the first and the second wearable devices, and wherein the updating modifies the weight of the weighted average.

8. A computer-implemented method for providing connecting relationships between wearable devices, the method comprising:
    measuring a base health parameter of a user via one or more sensors of a first wearable device;
    determining whether or not the base health parameter meets a certain predetermined threshold criterion;
    in response to the base health parameter meeting the certain predetermined threshold criterion, requesting measurement of a second health parameter of the user via one or more sensors of a second wearable device, wherein the second wearable device is selected by:
    determining a set of wearable devices that the user is wearing, wherein each wearable device in the set is configured to measure the second health parameter using a corresponding measuring method;
    determining, from a lookup table matching different health parameters with different measuring methods that is stored in memory of the first wearable device, the measuring method for each wearable device in the set to produce a set of measuring methods;
    selecting, from the determined set of measuring methods, the measuring method optimal for measuring the second health parameter; and
    selecting the wearable device with corresponding optimal measuring method as the second wearable device having the slave role for measuring the second health parameter;
    determining an alert action based on a combination of the base health parameter
    and the second health parameter; and generating a notification to the user based on the alert action.

9. The method of claim 8, wherein the optimal measuring method is determined based on a way of wearing of the corresponding wearable device.

10. A system for providing connecting relationships between wearable devices, the system comprising:

a first wearable device, comprising:

one or more sensors configured to measure a base vital sign of a user wearing the first wearable device;

a transceiver configured to receive a measurement of a second vital sign of the user from a second wearable device over a wireless communication network; and a processor configured to:

request measurement of the second vital sign from the second wearable device using the transceiver when the measurement of the base vital sign meets a predetermined threshold criterion;

determine an alert action based on a combination of the measurements of the base vital sign and the second vital sign, and further configured to generate a notification to the user based on the alert action.

11. The system of claim 10, further comprising:

the second wearable device, which comprises:

one or more sensors configured to measure the second vital sign of the user;

a transceiver configured to transmit the measurement of the second vital sign to the transceiver of the first wearable device.

12. The system of claim 11, wherein the first wearable device is assigned to a master role and the second wearable device is assigned to a slave role.

13. A non-transitory computer-readable storage medium, having embodied thereon a program executable by a processor to perform a method for providing on-demand wireless services between wearable devices, the method comprising:

measuring one or more base vital signs via one or more sensors of a first device;

determining that one or more of the measured base vital signs meets a certain predetermined threshold criterion;

if one or more of the measured base vital signs meeting a certain predetermined threshold criterion, then requesting one or more additional vital sign measurements from one or more secondary devices;

determining an alert action based on a combination of the measured base vital signs and the one or more additional vital sign measurements received from the one or more secondary devices; and generating a notification to the user based on the determined alert action.

* * * * *